United States Patent [19]

Schubert et al.

[11] Patent Number: 5,767,141

[45] Date of Patent: Jun. 16, 1998

[54] SUBSTITUTED PROPANE DERIVATIVES, A PROCESS FOR THEIR PREPARATION AND THE USE OF THE COMPOUNDS FOR TREATING DISEASES

[75] Inventors: Gerrit Schubert, Kelkheim; Horst Hemmerle, Lorsch; Peter Below, Frankfurt; Andreas Herling, Bad Camberg; Hans-Jörg Burger, Frankfurt, all of Germany

[73] Assignee: Hoechst Aktiengesellschaft, Frankfurt am Main, Germany

[21] Appl. No.: 400,952

[22] Filed: Mar. 8, 1995

[30] Foreign Application Priority Data

Mar. 10, 1994 [DE] Germany .................. 44 08 082.4

[51] Int. Cl.$^6$ ................ A61K 31/415; C07D 235/12; C07D 235/22; C07D 235/02
[52] U.S. Cl. ............... 514/393; 514/394; 514/512; 514/519; 514/520; 548/310.1; 548/303.1; 548/427; 548/215; 548/450; 548/253; 548/224; 548/472; 548/252; 548/350.1; 548/430; 548/509; 548/217; 548/304.4; 548/304.7; 549/49; 549/381; 549/471; 549/43; 549/385; 549/50; 549/76; 549/498
[58] Field of Search .................. 548/304.4, 304.7, 548/310.1, 303.1, 427, 215, 450, 253, 224, 472, 252, 350.1, 430, 509, 217; 514/394, 303, 393; 546/118, 138, 139, 142, 101, 114, 80, 79, 77, 133, 115, 279, 85, 250, 82, 117, 340, 170; 549/49, 381, 471, 43, 385, 50, 76, 498; 544/283, 349, 278, 350, 279, 117, 115, 344, 233

[56] References Cited

FOREIGN PATENT DOCUMENTS

| 4 617 093 | 3/1994 | Australia . |
| 0 587 087 A1 | 9/1995 | European Pat. Off. . |
| 0 587 088 A1 | 9/1995 | European Pat. Off. . |

OTHER PUBLICATIONS

Chem Abs 96:450372, Hattori, Augment of CA influx . . . , Mar. 20, 1996.
Chem Abs 96:421977, Glover, Propylene Glycol . . . , 1996.
Chem Abs 96:418066, Huth, Experimental Determ . . . , 1996.
Chem Abs 96:456634, Ren, Poly(ethylene–propylene glycol) . . . , 1996.
K. Heyns and A. Linkies, Chem. Ber. 108 (11), 3637–3644 (1975).

Primary Examiner—Mark L. Berch
Assistant Examiner—Bruck Kifle
Attorney, Agent, or Firm—Finnegan, Henderson, Farabow, Garrett & Dunner, L.L.P.

[57] ABSTRACT

Substituted propane derivatives, a process for their preparation and the use of the compounds for treating diseases Propane derivatives of the formula I

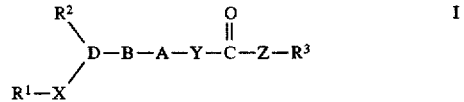

in which the radicals have the meanings stated in the description, a process for the preparation of these compounds, their use as pharmaceuticals, and pharmaceutical products are described. Also described are novel intermediates for preparing the compounds of the formula I.

10 Claims, No Drawings

SUBSTITUTED PROPANE DERIVATIVES, A PROCESS FOR THEIR PREPARATION AND THE USE OF THE COMPOUNDS FOR TREATING DISEASES

The syndrome of diabetes is characterized by elevated blood glucose levels. In the case of insulin-dependent or type I diabetes, the cause is death of the insulin-producing β cells in the pancreas; treatment is therefore by insulin administration (replacement therapy). Non-insulin-dependent or type II diabetes is, by contrast, characterized by a reduced effect of insulin on muscular and adipose tissue (insulin resistance) and increased glucose production in the liver. The causes of these metabolic disorders are still substantially unclear. The established therapy with sulfonyl ureas attempts to compensate the insulin resistance by increasing endogenous insulin release, but does not lead to normalization of the blood glucose level in every case and is unable to prevent progress of the disease; many type II diabetics eventually become, owing to "exhaustion" of the β cells, insulin-dependent and suffer from late damage such as cataracts, nephropathies and angiopathies. Novel therapeutic principles for the treatment of type II diabetes are therefore desirable.

The blood glucose concentration in the fasting state is determined by the glucose production in the liver. Various research groups have been able to show that elevation of the blood glucose levels in type II diabetes correlates with a proportionate increase in the glucose release from the liver. The glucose released from the liver into the blood may be produced either by breakdown of glycogen in the liver (glycogenolysis) or by gluconeogenesis.

Glucose 6-phosphate is the common end product both of gluconeogenesis and of glycogenolysis. The terminal step in the hepatic liberation of glucose from glucose 6-phosphate is catalyzed by glucose-6-phosphatase (EC 3.1.3.9). Glucose-6-phosphatase is a multienzyme complex which occurs in the endoplasmic reticulum (ER). This enzyme complex is composed of a glucose 6-phosphate translocase present in the ER membrane, of a glucose-6-phosphatase located on the luminal side of the endoplasmic reticulum, and of a phosphate translocase [for a review, see: Ashmore, J. and Weber G., "The Role of Hepatic Glucose-6-phosphatase in the Regulation of Carbohydrate Metabolism", in Vitamins and Hormones, Vol. XVII (Harris R. S., Marrian G. F., Thimann K. V., Edts.), 92–132, (1959); Burchell A., Waddell I. D., "The molecular basis of the hepatic microsomal glucose-6-phosphatase system", Biochim. Biophys. Acta 1092, 129–137, (1990)]. The available wide ranging literature shows that, under all investigated conditions which in animal experiments lead to elevated blood glucose levels, for example streptozotocin, alloxan, cortisone, thyroid hormones and starvation, the activity of this multienzyme complex is likewise elevated. Furthermore numerous investigations indicate that the increased glucose production observed in type II diabetics is linked to an elevated glucose-6-phosphatase activity. The importance of the glucose-6-phosphatase system for normal glucose homeostasis is further underlined by the hypoglycemic symptoms of patients with type Ib glycogen storage disease, who lack the translocase component of the glucose-6-phosphatase system.

A reduction in the glucose-6-phosphatase activity by suitable active substances (inhibitors) ought to lead to a corresponding reduction in the hepatic liberation of glucose. These active substances ought to be able to match the glucose production in the liver to the effective peripheral consumption. The resulting reduction in the blood glucose levels in type II diabetics in the fasting state should moreover also have a preventive effect in respect of late diabetic damage.

A number of non-specific inhibitors of glucose-6-phosphatase have been described in the literature, such as, for example, phlorrhizin [Soodsma, J. F., Legler, B. and Nordlie, R. C., J. Biol. Chem. 242, 1955–1960, (1967)], 5,5'-dithiobis-2-nitrobenzoic acid [Wallin, B. K. and Arion, W. J., Biochem. Biophys. Res. Commun. 48, 694–699, (1972)], 2,2'-diisothiocyanatostilbene and 2-isothiocyanato-2'-acetoxystilbene [Zoccoli, M. A. and Karnowski, M. L., J. Biol. Chem. 255, 1113–1119, (1980)]. The first therapeutically utilizable inhibitors of the glucose-6-phosphatase system are proposed in European Patent Applications No. 93 114 260.8 and No. 93 114 261.6.

The propane derivatives which are characterized in detail hereinafter are novel compounds which have not previously been described in the chemical and biological literature. We have now found that certain substituted propanes, such as, for example, Example 1, are inhibitors of the glucose-6-phosphatase system.

The invention therefore relates to propane derivatives of the formula I

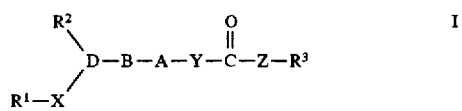

in which the radicals have the following meanings:

D-B-A: Propylene which is optionally substituted by 1 to 3 groups selected from $C_1$-$C_3$-alkyl, ω-hydroxy-($C_1$-$C_4$) -alkyl, OH, O—$C_1$-$C_4$-alkyl, phenyl and phenyl-$C_1$-$C_3$-alkyl, $R^1$: CN, COOH, a COOH group protected with a protective group, $C_1$-$C_4$-alkanoyl, $SO_3$—$C_1$-$C_4$-alkyl, $SO_3H$, $SO_2NR^5R^6$, PO(OH)$_2$, PO(OH)(O—$C_1$-$C_4$-alkyl), PO(O—$C_1$-$C_4$-alkyl)$_2$, 5-tetrazolyl, $R^2$: $C_1$-$C_{10}$-alkyl $(R^8)_n$, O—$C_1$-$C_{10}$-alkyl $(R^8)_n$, $C_2$-$C_{10}$-alkenyl $(R^8)_n$, O—$C_3$-$C_{10}$-alkenyl $(R^8)_n$, $C_2$-$C_{10}$-alkynyl $(R^8)_n$, O—$C_3$-$C_{10}$-alkynyl $(R^8)_n$, S—$C_1$-$C_{10}$-alkyl $(R^8)_n$, S—$C_3$-$C_{10}$-alkenyl $(R^8)_n$, S—$C_3$-$C_{10}$-alkynyl $(R^8)_n$, NH—$C_1$-$C_{10}$-alkyl $(R^8)_n$, NH—$C_3$-$C_{10}$-alkenyl $(R^8)_n$ or NH—$C_3$ –$C_{10}$-alkynyl $(R^8)_n$, where $R^8$ is optionally in each case substituted by $R^9$;

$R^3$, $R^8$ and $R^{10}$: alkyl having 1 to 10 carbon atoms, cycloalkyl having 3–8 ring carbon atoms, phenyl, naphthyl, phenanthryl, pyridyl, thienyl, furyl, pyrimidyl, indolyl, imidazolyl, coumarinyl, phthalimidyl, quinolyl, piperazinyl, tetrazolyl, triazolyl, oxazolyl or their thieno-, pyridino-, pyrimidino-, pyrazino-, pyridazino- or benzofused derivatives, where the aromatic or heteroaromatic system can be substituted one or more times, identically or differently, by F, Cl, Br, I, OH, $CF_3$, —$NO_2$, CN, $C_1$-$C_4$-alkoxy, $C_1$-$C_4$-alkyl, $NR^5R^6$, phenyl, benzyl, thienyl, furyl, imidazolyl, pyridyl, O-phenyl or O-benzyl, and $R^3$, $R^8$ and $R^{10}$ are identical or different;

$R^4$: $C_1$-$C_4$-alkyl, phenyl or benzyl;

$R^5$ and $R^6$: H, $C_1$-$C_4$-alkyl, $C_1$-$C_4$-alkanoyl, phenyl which is optionally substituted by F, Cl, Br, I, OH, O—$C_1$-$C_4$-alkyl, $CF_3$, —$NO_2$ or CN, where $R^5$ and $R^6$ are identical or different, or $R^5$ and $R^6$ form, together with the nitrogen atom, a 4- to 10-membered, saturated heterocyclic ring in which one $CH_2$ group can optionally be replaced by O, S or $NR^7$.

$R^7$: H, $C_1$-$C_4$-alkyl, phenyl or benzyl;

$R^9$: phenyl, naphthyl, phenanthryl, pyridyl, thienyl, furyl, pyrimidyl, indolyl, imidazolyl, coumarinyl, phthalimidyl, quinolyl, piperazinyl, tetrazolyl, triazolyl, oxazolyl or their thieno- or benzo-fused derivatives, where the aromatic or heteroaromatic system can be substituted one or more times, identically or differently, by F, Cl, Br, I, OH, $CF_3$, $-NO_2$, CN, $C_1$-$C_4$-alkoxy, $C_1$-$C_4$-alkyl, $C_2$-$C_4$-alkenyl, $NR^5R^6$, phenyl, benzyl, thienyl, furyl, imidazolyl, pyridyl, O-phenyl or O-benzyl;

X: $(CH2)_m$, $-CH=CH-$, $-C\equiv C-$, $-CH_2-O-CH_2-$, $-CH_2-S-CH_2-$ or

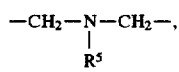

Y: $(CH_2)_m$, O, S, $NR^5$,

Z: $(CH_2)_m$, S, O, S—$C_1$-$C_{10}$-alkyl, O—$C_1$-$C_{10}$-alkyl, $CH=CH$, $CH=CF$, $CH=CCl$, $CH=CBr$, $CH_2-CO$, $CH_2-CHF$, $CH_2-CHCl$, $CH_2-CHBr$, $CH_2-CHI$, $C_3$-$C_{10}$-cycloalkylene, $C_3$-$C_{10}$-cycloalkenylene, where 1 to 3 ring carbon atoms can be replaced by sulfur, oxygen or nitrogen atoms, $COOR^4$, $C\equiv C$, $CH=C(C_1$-$C_4$-alkyl), $CH=C(CN)$, $CH=C(NR^5R^6)$, $CH=C(C_1$-$C_4$-alkanoyl), $CH=C(R^{10})$, $NR^5$ and, when Y is oxygen, it is possible for

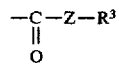

together to represent an amino-acid residue selected from the group consisting of Ala, Arg, Asn, Asp, Cys, Gln, Glu, Gly, His, Ile, Leu, Lys, Phe, Pro, Ser, Thr, Trp, Tyr and their derivatives protected by customary protective groups, n: zero, 1 or 2 m: zero, 1, 2, 3 or 4.

The compounds of the formula I according to the invention are able if they contain a carboxyl group to form salts with inorganic or organic bases. The invention therefore also relates to the physiologically tolerated salts of compounds of the formula I.

The compounds of the formula I according to the invention contain a number of stereocenters. The invention relates to all possible enantio- and diastereomers. They are all represented by the formula I.

Unless indicated otherwise, the following apply to the statements hereinbefore and hereinafter:

The alkyl, alkanoyl and alkoxy radicals indicated under $R^1$, $R^3$, $R^4$, $R^5$, $R^6$, $R^7$, $R^8$, $R^{10}$ and Z are straight-chain or branched.

The alkyl, alkenyl and alkynyl groups indicated under $R^2$ and $R^9$ are straight-chain, branched or cyclic, it also being possible for only part of the radical to form a ring.

One of the $CH_2$ groups can be replaced by O, S, SO, $SO_2$ or $NR^5$, $R^8$ can be substituted by $R^9$ and, when n=2, the two $R^8$ radicals are identical or different. Unsaturated radicals are mono- or polyunsaturated.

A COOH radical protected by a protective group means COO—$C_1$-$C_{10}$-alkyl (unbranched or branched or cyclic), COO—$CH(R^4)$—O—$C_1$-$C_4$-alkanoyl (unbranched or branched), COO-benzyl, COO-phenyl, $CONH_2$, $CONH$—$C_1$-$C_{10}$-alkyl (unbranched and branched), —$CONR^5R^6$, where $R^4$, $R^5$ and $R^6$ have the stated meanings.

Alcohol protective groups are: substituted ethers such as methoxymethyl, methylthiomethyl, t-butylthiomethyl, benzyloxymethyl, p-methoxybenzyloxymethyl, t-butoxymethyl, siloxymethyl, 2-methoxyethoxymethyl, 1-ethoxyethyl, allyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl.

Protective groups for amino acids are:
a) carbamates such as methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl, 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkylthio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl, t-amyl, S-benzylthiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di-(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phonylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl and 2,4,6-trimethylbenzyl.

b) Urea derivatives such as 10-phenothiazinylcarbonyl derivatives, N'-p-toluenesulfonylaminocarbonyl and N'-phenylaminothiocarbonyl.

c) Amides such as N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivatives, N-benzoyl and N-p-phenylbenzoyl.

Preferred compounds of the formula I are those in which $R^1$ is CN, COOH, a COOH group which is protected by a protective group, or $C_1$-$C_4$-alkanoyl, and the other radicals have the abovementioned meanings.

Particularly preferred compounds of the formula I are those in which the radicals have the following meanings:

$R^1$: CN, COOH, a COOH group protected with a protective group or $C_1$-$C_4$-alkanoyl or 5-tetrazolyl, $R^2$: O—$C_1$-$C_{10}$-alkyl$(R^8)_n$ (n=0, 1, 2), where the alkyl moiety is unbranched, branched or cyclic, and one of the $CH_2$ groups can be replaced by O, and $R^8$ can be substituted by $R^9$, and, when n=2, the two $R^8$ radicals are identical or different, O—$C_3$-$C_{10}$-alkenyl$(R^8)_n$ (n=0, 1, 2), where the alkenyl moiety is unbranched, branched or cyclic, one of the $CH_2$ groups can be replaced by O, S, SO, $SO_2$ or $NR^5$, and is mono- or polyunsaturated, and $R^8$ can be substituted by $R^9$, and, when n=2, the two $R^8$ radicals are identical or different,
O—$C_3$-$C_{10}$-alkynyl($R^8$) (n=0, 1, 2), where the alkynyl
moiety is unbranched, branched or cyclic, and is mono-
or polyunsaturated, and one of the $CH_2$ groups can be
replaced by O, S, SO, $SO_2$ or $NR^5$, and $R^8$ can be
substituted by $R^9$, and, when n=2, the two $R^8$ radicals
are identical or different, $R^3$ to $R^{10}$ have the abovementioned meanings, X: $(CH_2)_m$, (m=0, 1, 2, 3, 4) CH=CH, C≡C, $CH_2OCH_2$, $CH_2SCH_2$ Y: $(CH_2)_m$, (m=0, 1, 2, 3, 4) O, S, $NR^5$, Z: $(CH_2)_m$, (m=0, 1, 2, 3, 4) S, O, S—$C_1$-$C_{10}$-alkyl, (unbranched or branched), CH=CH, CH=CF, CH=CCl, CH=CBr, $CH_2$—C(O), $CH_2$—CHF, $CH_2$—CHCl, $CH_2$—CHBr, $CH_2$—CHI, $C_3$-$C_{10}$-cycloalkylene, $C_3$-$C_{10}$-cycloalkenylene, $COOR^4$, C≡C, CH=C($C_1$-$C_4$-alkyl) (unbranched or branched), CH—C(CN), CH=C($R^{10}$), $NR^5$. The propyl radical D-B-A is preferably unsubstituted or substituted on B by 2 methyl groups.

The compounds of the formula I according to the invention are able when they contain a carboxyl group to form salts with inorganic or organic bases. Preferred salts are those with inorganic bases, particularly the physiologically acceptable alkali metal salts, especially sodium and potassium salts.

The compounds of the formula I inhibit the glucose-6-phosphatase system of the liver in mammals. The compounds are therefore suitable as pharmaceuticals. The invention therefore also relates to pharmaceuticals based on compounds of the formula, where appropriate in the form of the physiologically tolerated salts.

The invention furthermore relates to the use of compounds of the formula I or of the salts for the treatment of diseases associated with an increased activity of the glucose-6-phosphatase system.

The invention also relates to the use of compounds of the formula I or of the salts for the treatment of diseases associated with an increased glucose production in the liver.

The invention additionally relates to the use of compounds of the formula I or of the salts for the treatment of type II diabetes (non-insulin-dependent or adult-onset diabetes).

The invention furthermore comprises the use of compounds of the formula I or of the salts for the production of pharmaceuticals for the treatment of diabetes and other disorders characterized by an increased output of glucose from the liver or an increased activity of the glucose-6-phosphatase system.

The effect of the compounds according to the invention on the glucose-6-phosphatase system was investigated in an enzyme assay in liver microsomes.

To prepare the microsome fraction containing the glucose-6-phosphatase, fresh liver organs from male Wistar rats were used and were processed as described in the literature [Canfield, W. K. and Arion, W. J., J. Biol. Chem. 263, 7458–7460, (1988)]. This microsome fraction can be stored at −70° C. for at least 2 months without significant loss of activity.

The glucose-6-phosphatase activity was detected as indicated in the literature (Arion, W. J. in Methods Enzymol. 174, Academic Press 1989, pages 58–67) by determination of the phosphate liberated from glucose 6-phosphate. 0.1 ml of assay mixture contained glucose 6-phosphate (1 mmol/l), the test substance, 0.1 mg of microsome fraction and 100 mmol/l HEPES buffer (4-(2-hydroxyethyl)piperazine-1-ethanesulfonic acid), pH 7.0. The reaction was started by adding the enzyme. After 20 minutes at room temperature, the reaction was stopped by adding 0.2 ml of phosphate reagent. The sample was incubated at 37° C. for 30 min, and the absorption (A) of the blue color was subsequently measured at 570 nm. The inhibitory activity of the test substance emerged from comparison with a control reaction which contained no test substance according to the formula $$\text{Percent inhibition} = \frac{A\text{ (control)} - A\text{ (test substance)}}{A\text{ (control)}} \times 100$$

When necessary, the inhibitory effect of the test substance was measured as a function of the test substance concentration used, and the concentration for 50% inhibition of enzyme activity ($IC_{50}$) was calculated therefrom.

The $IC_{50}$ was determined for the compound specified below:

Compound from Example 1:

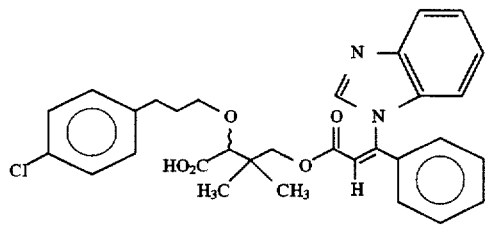

(±)-4-(3Z-benzimidazol-1-yl-3-phenylpropenoyloxy)-2-(4-chlorophenylpropyloxy)-3,3-dimethylbutanoic acid $IC_{50}$=4 μM The compounds of the formula I according to the invention in which the radicals $R^2$=O-alkyl($R^8$)$_n$, O-alkenyl($R^8$)$_n$ or O-alkynyl($R^8$)$_n$ and Y is O can be prepared by route A shown in the following diagram.

Process A

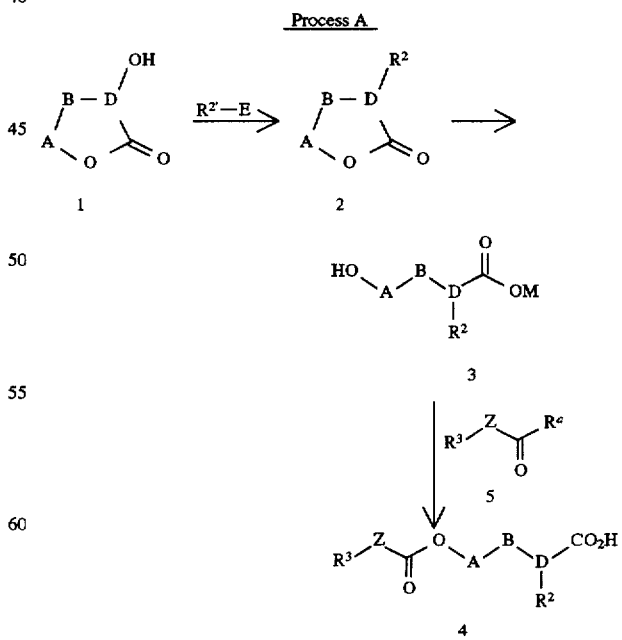

M: alkali metal $R^a$: Cl, Br,

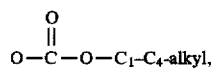

imidazolyl, triazolyl or tetrazolyl A

E: chlorine, bromine, iodine, sulfonate $R^{2'}$: alkyl$(R^8)_n$, alkenyl$(R^8)_n$ or alkynyl$(R^8)_n$ (4=formula I, $R^2$=O—$C_1$-$C_{10}$-alkyl$(R^8)_n$, O—$C_3$-$C_{10}$-alkenyl $(R^8)_n$ or O—$C_3$-$C_{10}$-alkynyl$(R^8)_n$, Y=O, X=(CH$_2$)$_m$ with m=zero, $R^1$=COOH, Z, $R^3$, $R^8$ and n as indicated for formula I).

Starting compound 1 is known or is prepared by processes known from the literature. Compound 1 is deprotonated with a strong base such as potassium tert-butoxy, sodium hydride or potassium hydride and, to introduce $R^2$, reacted with appropriate halides, trifluorosulfonic esters, methylsulfonic esters or p-toluenesulfonic esters, advantageously in polar aprotic solvents such as dimethylformamide, dimethyl sulfoxide or tetrahydrofuran, resulting in compound 2. Preferably used as base is sodium hydride and as solvent is dimethylformamide.

The reaction from 1 to 2 is carried out at temperatures from −20° C. to the boiling point of the solvent used. A temperature range from −10 to 60° C. is preferred, particularly from 0° to 30° C.

The preferred embodiment of the reaction 1 to 2 takes place in dimethylformamide in the presence of sodium hydride or potassium hydride at temperatures from 0° to 60° C. In this case, the reaction is advantageously carried out with exclusion of moisture under a protective gas (nitrogen or argon).

The starting materials which correspond to the radical $R^2$ and are required for the reaction from 1 to 2 can be prepared by standard processes known to the skilled person. These comprise structures of the type $R^{2'}$-E with the restriction specified for process A (although without the linking oxygen atom). The meaning of E is, for example, a leaving group such as Cl, Br, I or OSO$_2$R (R=CH$_3$, Ph, tolyl, CF$_3$).

A further step in process A is hydrolysis of the lactone 2 to the alkali metal salt 3 with alkali metal hydroxides such as lithium hydroxide, sodium hydroxide or potassium hydroxide. The reaction is advantageously carried out in protic or aprotic solvents such as lower alcohols, tetrahydrofuran or dioxane, and the use of dioxane is preferred.

The reaction from 2 to 3 is carried out at temperatures from −20° C. to the boiling point of the solvent used. A temperature range from −10° to 60° C. is preferred, in particular from 0° to 30° C.

A further step is the reaction from 3 to 4 in which the radical $R^3$—Z—C(O)— is attached to 3. For this purpose, 3 is reacted in an aprotic organic solvent such as, for example, tetrahydrofuran, dimethylformamide, dichloromethane, pyridine or dimethyl sulfoxide with a compound $R^3$—Z—C(O)—$R^a$ (5) where $R^a$ can be, for example, Cl, Br, OC(O)—$C_1$-$C_4$-alkyl, imidazolyl, triazolyl or tetrazolyl, with imidazolyl and triazolyl being particularly preferred. The reaction is particularly preferably carried out in dimethylformamide in the presence of a base such as, for example, sodium hydride, potassium hydride, 4-dialkylaminopyridine or tert. amines, but especially of sodium hydride.

The reaction 3 to 4 is carried out at temperatures from −20° C. to the boiling point of the solvent used. A temperature range from −10° to 60° C. is preferred, in particular from 0° to 30° C.

Compounds $R^3$—Z—C(O)—$R^a$ (5) can be prepared by standard processes known to the skilled person.

A preferred embodiment of the reaction 3 to 4 comprises reacting 3 with sodium hydride in dimethylformamide and subsequently adding a solution of $R^3$—Z—C(O)-imidazole (5) in dimethylformamide at 0° to 20° C., advantageously with exclusion of moisture under protective gas (argon or nitrogen).

The resulting compounds of the formula I according to the invention are able when they contain a carboxyl group to form salts with inorganic or organic bases. Salts of this type with inorganic bases are therefore also preferred, especially the physiologically acceptable alkali metal salts, in particular sodium and potassium salts.

The esters indicated for $R^1$ can be prepared from the alkali metal salts of the compounds of the formula I with a carboxyl group. For this purpose, compound 4 is reacted in an inert organic solvent such as tetrahydrofuran, dimethyl sulfoxide, preferably dimethylformamide, at −10° to 60° C., for example with a $C_1$-$C_4$-alkyl halide, preferably $C_1$-$C_4$-alkyl iodide, benzyl bromide or $C_1$-$C_4$-alkanoyl-O—CH($R^4$)—Br or $C_1$-$C_4$-alkanoyl-O—CH($R^4$)—I to give the compounds of the formula I according to the invention with an ester group as $R^1$ and X=(CH$_2$)$_m$ m=0 with the details mentioned for process A.

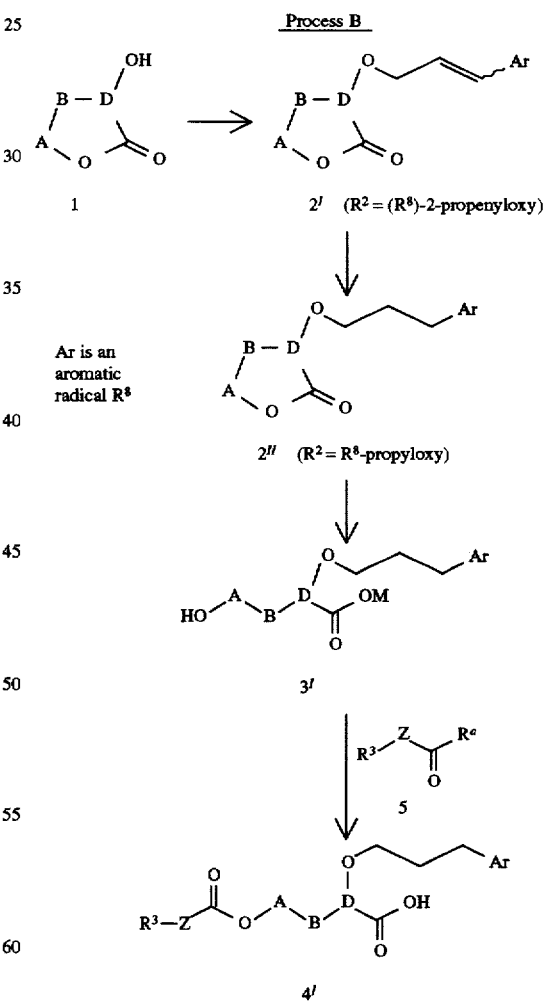

($4'$=formula I, $R^2$=$R^8$-propyloxy, other meanings compare process A).

Process B comprises deprotonating compound 1 with a strong base such as potassium tert-butoxide, sodium hydride or potassium hydride and, to introduce $R^2$ in the stated meaning, reacting with appropriate halides, trifluorosulfonic esters, methylsulfoniic esters or p-toluenesulfonic esters, advantageously in polar aprotic solvents such as dimethylformamide, dimethyl sulfoxide or tetrahydrofuran, resulting in compound $2'$. Preferably used as base is sodium hydride and as solvent dimethylformamide.

The reaction from 1 to $2'$ is carried out at temperatures from $-20°$ C. to the boiling point of the solvent used. A temperature range from $-10°$ to $60°$ C. is preferred, in particular from $0°$ to $30°$ C.

The preferred embodiment of the reaction 1 to $2'$ takes place in dimethylformamide in the presence of sodium hydride or potassium hydride at temperatures from $0°$ to $60°$ C. In this case, the reaction is advantageously carried out with exclusion of moisture under a protective gas (nitrogen or argon).

The starting materials which correspond to the $R^2$ radical and are required for the reaction from 1 to $2'$ can be prepared by standard processes known to the skilled person. These comprise structures of the type $R^{2'}$-E with the restriction specified for process B (although without the linking oxygen atom). The meaning of B is, for example, a leaving group such as Cl, Br, I or $OSO_2R$ ($R=CH_3$, Ph, tolyl, $CF_3$).

$2''$ ($R^2=R^8$-propyloxy) can be prepared from $2'$ by hydrogen in the presence of hydrogenation catalysts. The reactions are carried out in ethyl acetate or methanol under atmospheric pressure. The reaction is carried out with a catalyst, for example rhodium on aluminum oxide, at temperatures from $0°$ C. to the boiling point of the solvent used. Ethyl acetate is preferred as solvent, and a temperature range from $20°$ to $50°$ C. is preferred, particularly from $20°$ to $30°$ C.

A further step in process B is hydrolysis of the lactone $2''$ to the alkali metal salt 31 with alkali metal hydroxides such as lithium hydroxide, sodium hydroxide or potassium hydroxide. The reaction is advantageously carried out in protic or aprotic solvents such as lower alcohols, tetrahydrofuran or dioxane, and the use of dioxane is preferred.

The reaction from $2''$ to $3'$ is carried out at temperatures from $-20°$ C. to the boiling point of the solvent used. A temperature range from $-10°$ to $60°$ C. is preferred, particularly from $0°$ to $30°$ C.

A further step is the reaction from $3'$ to $4'$ in which the radical $R^3$—Z—C(O)— is attached to $3'$. For this purpose, $3'$, is reacted in an aprotic organic solvent such as, for example, tetrahydrofuran, dimethylformamide, dichloromethane, pyridine or dimethyl oulfoxide with a compound $R^3$—Z—C(O)—$R^a$ (5) where $R^a$ can be, for example, Cl, Br, OC(O)—$C_1$-$C_4$-alkyl, imidazolyl, triazolyl or tetrazolyl, with imidazolyl and triazolyl being particularly preferred. It is particularly preferred to carry out the reaction in dimethylformamide in the presence of a base such as, for example, sodium hydride, potassium hydride, 4-dialkylaminopyridine or tert. amines, but especially of sodium hydride.

The reaction $3'$ to $4'$ is carried out at temperatures from $-20°$ C. to the boiling point of the solvent used. A temperature range from $-10°$ to $60°$ C. is preferred, in particular from $0°$ to $30°$ C.

The compounds $R^3$—Z—C(O)—$R^a$ (5) can be prepared by standard processes known to the skilled person.

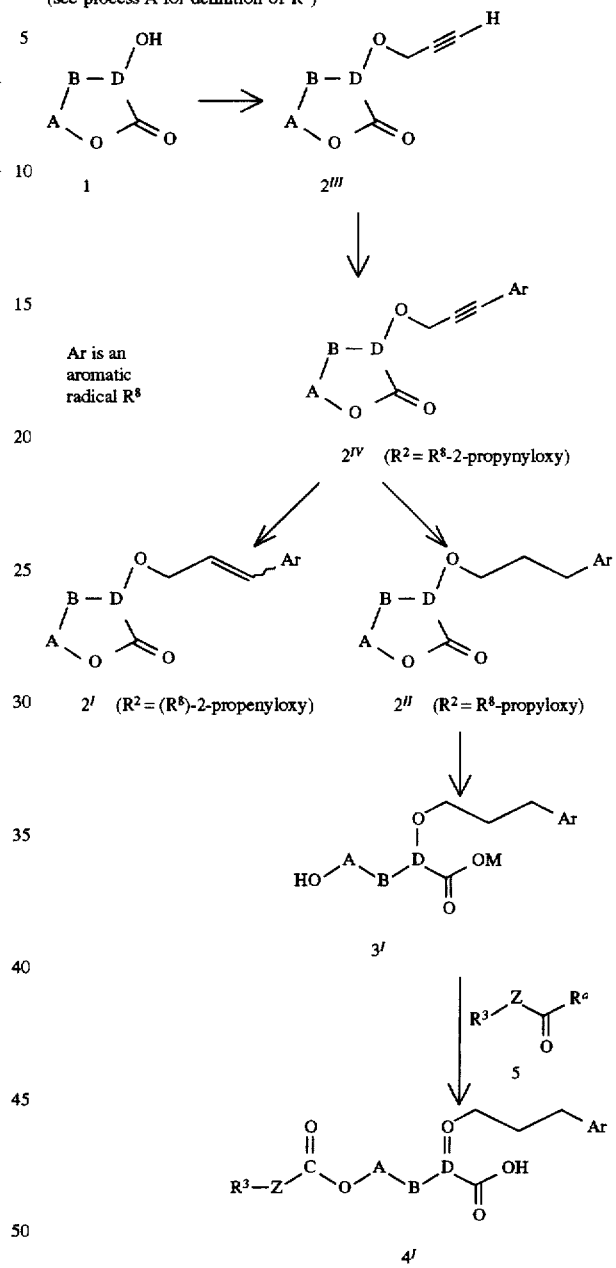

Process C (see process A for definition of $R^a$)

Ar is an aromatic radical $R^8$ $2^{IV}$ ($R^2=R^8$-2-propynyloxy)

$2'$ ($R^2=(R^8)$-2-propenyloxy)   $2''$ ($R^2=R^8$-propyloxy)

An alternative process to A for a number of compounds of the formula I according to the invention is process C. For $R^2=O$—$C_3$-alkynyl($R^8$), the intermediate can be $2'''$ where $R^2$=2-propynyloxy. In this case, $2'''$ ($R^2$=2-propynyloxy) is reacted in an inert organic solvent such as, for example, toluene, benzene or n-hoptane with catalysis by a palladium complex and copper(I) halide, particularly copper(I) iodide, with an aryl halide, particularly aryl bromide or aryl iodide, to give $2^{IV}$ ($R^2=R^8$-2-propynyloxy). For this purpose it is necessary to add a base such as, for example, primary, secondary or tertiary amines, particularly triethylamine. It is also possible optionally for the base simultaneously to act as solvent and to dispense with addition of another organic solvent.

The reaction $2'''$ ($R^2$=2-propynyloxy) to $2^{IV}$ ($R^2=R^8$-2-propynyloxy) is carried out at temperatures from $-20°$ C. to the boiling point of the solvent used. A temperature range from 20° to 90° C. is preferred, in particular from 60° to 80° C.

It is possible to use as palladium complex, for example, the complex ditriphenylphosphinepalladium dichloride which can be prepared in situ from palladium dichloride and triphenylphosphine, or the complex ditriphenylphosphinepalladium diacetate which can be obtained in the same way from palladium(II) acetate, and ditriphenylphosphinepalladium dichloride is preferred.

$2'$ ($R^2$=$R^8$-2-propenyloxy) or $2''$ ($R^2$=$R^8$-2-propyloxy) can be prepared specifically from $2^{IV}$ ($R^2$=$R^8$-2-propynyloxy) by hydrogenation catalysts. The reactions are carried out in ethanol or pyridine under a hydrogen atmosphere under atmospheric pressure.

The reaction $2^{IV}$ ($R^2$=$R^8$-2-propynyloxy) to $2'$ ($R^2$=$R^8$-2-propenyloxy) is carried out with a palladium on barium sulfate catalyst at temperatures from 0° C. to the boiling point of the solvent used. Pyridine is preferred as solvent, and a temperature range from 20° to 50° C. is preferred, in particular from 20° to 30° C.

The reaction $2^{IV}$ ($R^2$=($R^8$)-2-propynyloxy) to $2''$ ($R^2$=($R^8$)propyloxy) is carried out with palladium on carbon as catalyst in ethanol at temperatures from −20° C. to the boiling point of the solvent used. A temperature range from 20° to 50° C. is preferred, in particular from 20° to 30° C.

The further reactions of $2'$ to $4'$, and $2''$ to $4'$, i.e. to the compounds of the formula I, are described in detail under process B.

The compounds $2''$, and $2^{IV}$ can also be converted without hydrogenation steps into compounds of the formula I according to the invention ($R^2$=O—$C_3$-alkenyl($R^8$) or $R^2$=O—$C_3$-alkynyl($R^8$)) in analogy to process A (steps 2 and 3).

Compound 5, which is used, for example, in the synthesis of the compounds of Examples 1 to 3, is expediently prepared by process I, II, III as described hereinafter.

Process I

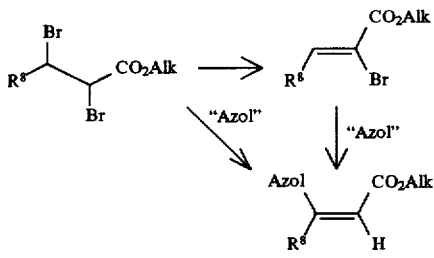

Process II

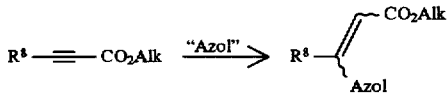

Process III

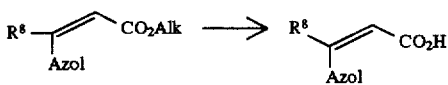

Alk is $C_1$–$C_4$-alkyl

Azol is $R^{10}$ meaning imidazolyl, indolyl, piperazinyl, tetrazolyl, triazolyl or their thieno-, pyridino-, pyrimidino-, pyrazino-, pyridazino- or benzo-fused derivatives.

Process I

Preparation of β-azol-substituted methyl cinnamates

A mixture of 50 g of methyl 2,3-dibromo-3-phenylpropanoate, 100 ml of triethylamine and 500 ml of toluene is heated to boiling for 1 h and subsequently cooled to room temperature and filtered. The filtrate is evaporated in vacuo, and the α-bromocinnamic acid obtained in this way is used further without purification. 0.2 mol of the azol derivative dissolved in 150 ml of anhydrous DMF is added dropwise with stirring to a suspension of 4.7 g of NaK (80% in mineral oil) in 100 ml of anhydrous DMF. The temperature of the mixture is maintained below 35° C. during this by cooling with ice. After the addition is complete, the mixture is stirred at room temperature for 1 h. The previously prepared α-bromocinnamic acid is dissolved in 200 ml of anhydrous DMF and, while cooling with ice, the solution of the azol sodium salt is added dropwise with stirring. After stirring at room temperature for two hours, 10.8 ml of glacial acetic acid are added, the mixture is stirred into 1.5 l of ice-water and extracted several times with ethyl acetate, and the organic phases are washed with water. The organic phases are dried and evaporated in vacuo, and the residue is purified by column chromatography on silica gel (mobile phase: n-heptane/ethyl acetate) or recrystallization.

Process II

Preparation of β-azol-substituted ethyl cinnamates

A mixture of 20 g of ethyl phenylpropiolate, 0.11 mol of azol derivative and 15 ml of anhydrous DMF is stirred at room temperature while passing in argon. A spatula of NaH (80% in mineral oil) is added. When evolution of hydrogen is finished, the mixture is heated to 100°–150° C. (bath temperature) and the reaction is followed by TLC (mobile phase n-heptane/ethyl acetate). After the reaction is complete, the mixture is cooled to room temperature and concentrated in vacuo, and the residue is recrystallized from n-heptane or diluted with a little n-heptane/ethyl acetate and purified by column chromatography on silica gel (mobile phase: n-heptane/ethyl acetate).

Process III

Preparation of β-azol-substituted cinnamic acids from β-azol-substituted cinnamic esters 6.4 mmol of β-azol-substituted methyl or ethyl cinnamates are suspended in a solution of 0.77 g of NaOH in 50 ml of water and 10 ml of methanol, and the mixture is stirred at room temperature until complete reaction is evident in the TLC (mobile phase n-heptane/ethyl acetate) and a clear solution is produced. This is concentrated in vacuo, diluted with about 50 ml of water and adjusted to pH 2–3 with 2N HCl while cooling in ice. If a solid precipitates, it is filtered off with suction and dried in vacuo. Otherwise, the mixture is extracted several times with $CH_2Cl_2$, the organic phases are dried and evaporated in vacuo, and the residue is purified by recrystallization or chromatography on silica gel (mobile phase: n-heptane/ethyl acetate/glacial acetic acid).

The invention further relates to pharmaceuticals which contain one or more compounds of the formula I according to the invention and/or their pharmacologically acceptable salts.

The pharmaceuticals are produced by processes known per se and familiar to the skilled person. The pharmacologically active compounds according to the invention (=active substance) are used as pharmaceuticals either as such or, preferably, in combination with suitable pharmaceutical ancillary substances in the form of tablets, coated tablets, capsules, suppositories, emulsions, suspensions, granules, powders, solutions or products with protracted release of active substance, with the content of active substance advantageously being from 0.1 to 95%.

The ancillary substances suitable for the desired pharmaceutical formulation are familiar to the skilled person on the basis of his expert knowledge. Besides solvents, gel formers, suppository bases, tablet ancillary substances and other active substance vehicles it is possible to use, for example, antioxidants, dispersants, emulsifiers, foam suppressants, flavorings, preservatives, solubilizers or colorants.

The active substances can be administered topically, orally, parenterally or intravenously, with the preferred form of administration depending on the disease to be treated. Oral administration is preferred.

For a form for oral use, the active compounds are mixed with the additives customary for this purpose, such as excipients, stabilizers or inert diluents, and converted by conventional methods into suitable administration forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose or starch, especially corn starch. Preparation may moreover take place either as dry or as wet granules. Suitable oily excipients or solvents are vegetable or animal oils, such as sunflower oil or fish liver oil.

For subcutaneous or intravenous administration, the active compounds or their physiologically tolerated salts are converted, if required with the substances customary for this purpose, such as solubilizers, emulsifiers or other ancillary substances, into solution, suspension or emulsion. Examples of suitable solvents are water, physiological saline solution or alcohols, for example ethanol, propanol, glycerol, besides sugar solutions such as glucose or mannitol solutions, or else a mixture of various solvents.

Pharmaceutical products suitable for topical and local use are eye drops which contain the active compound in aqueous or oily solution. Suitable for use in the nose are aerosols and sprays, and coarse powders which are administered by rapid inhalation through the nostrils, and, in particular, nose drops which contain the active compounds in aqueous or oily solution.

The dosage of the active substance of the formula I to be administered and the frequency of administration depend on the strength of action and duration of action of the compound according to the invention used; in addition on the nature and severity of the disease to be treated and on the sex, age, weight and individual ability to respond of the mammal to be treated. On average, the recommended daily dose of a compound according to the invention for a mammal weighing about 75 kg—primarily a human—is in the range from about 10 to 500 mg, preferably from about 25 to 250 mg, it being possible for administration to take place if required in several doses a day.

The following examples are intended to illustrate the present invention without, however, restricting its scope.

EXAMPLE I (Process B)

(±)-4-(3Z-(1-Benzimidazolyl)-3-phenylpropenoyloxy)-2-(4-chlorophenylpropyloxy)-3,3-dimethylbutanoic acid (I)

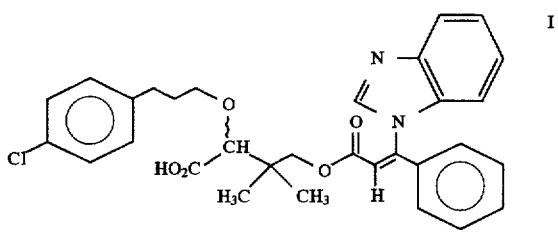

Stage 1

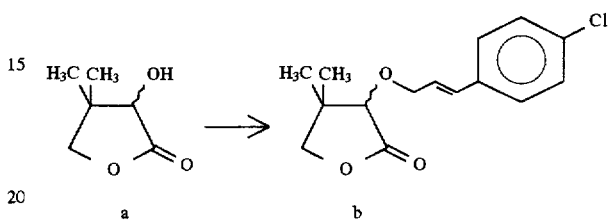

3.3 g of 80 percent NaH in mineral oil are added in portions over the course of one hour to a solution of 13.0 g of DL-pantolactone (a) in 300 ml of anhydrous DMF while stirring at 0° C. under argon. When gas evolution is finished, a solution of 4-chlorocinnamoyl bromide in 100 ml of anhydrous DMF is added dropwise over the course of 30 minutes. The progress of the reaction is followed by TLC (eluent: heptane/ethyl acetate). After the reaction is complete, the mixture is evaporated in vacuo, poured into ice-cold concentrated $NH_4Cl$ solution and extracted several times with $CH_2Cl_2$, and the organic phases are dried and evaporated. The residue is purified by chromatography on silica gel (eluent: heptane/ethyl acetate mixture) and used in stage 2.

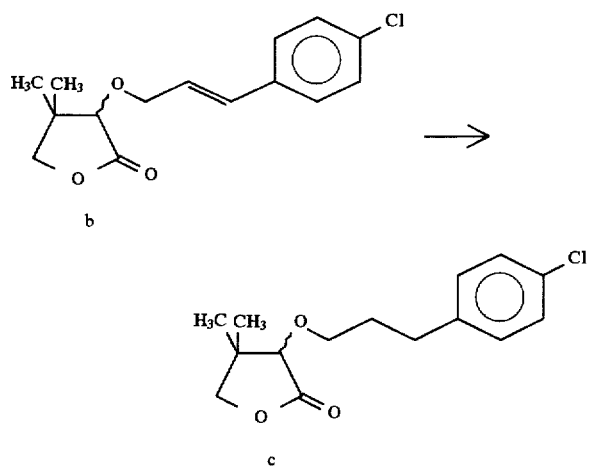

Stage 2

7.1 g of 5 percent rhodium on aluminum oxide hydrogenation catalyst are added to a solution of 21.6 g of compound b in 1,200 ml of ethyl acetate, and hydrogenation is carried out in a hydrogenation apparatus as far as the theoretical $H_2$ uptake. The catalyst is then removed by filtration and the filtrate is evaporated.

Stage 3

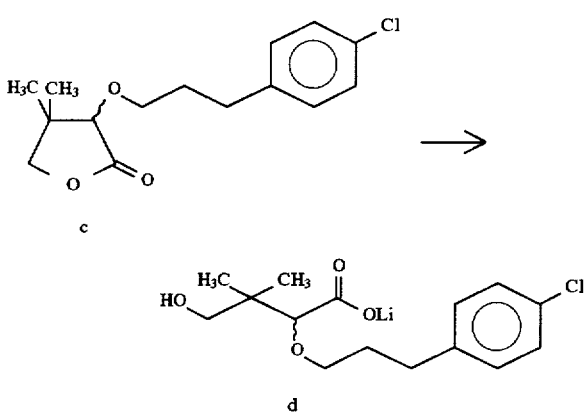

Dioxane is added to a mixture of 2.82 g of compound c and 11 ml of a 1 molar LiOH solution in water until the mixture is substantially homogeneous. The progress of the reaction is followed by TLC (eluent: heptane/ethyl acetate mixture). After the reaction is complete, the mixture is evaporated in vacuo, the residue is taken up in anhydrous DMF, and evaporation is repeated.

Stage 4

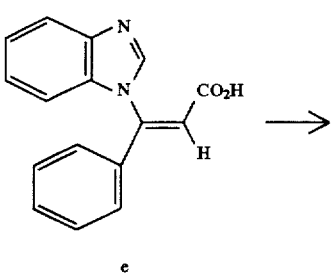

1.18 g of 1,1-carbonyldiimidazole are added to a solution of 1.72 g of carboxylic acid e (compare process I, II or III for preparation) in 20 ml of anhydrous DMF, and the mixture is stirred at 50° to 60° C. under argon for 5 hours. The product is used directly, without working up, in stage 5.

Stage 5

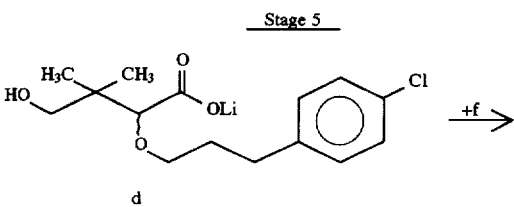

Stage 5 -continued

Initially 0.94 g of compound 10 prepared as in stage 3 is added to the solution of compound f prepared in stage 4 under argon, and subsequently 100 mg of 80 percent NaH in mineral oil are added, and the mixture is stirred at room temperature for about 1 hour. The reaction is followed by TLC (eluent: ethyl acetate/heptane/glacial acetic acid mixture). For working up, the mixture is poured onto ice-cold saturated NH$_4$Cl solution and extracted several times with CH$_2$Cl$_2$. The organic phases are dried and evaporated in vacuo, and the residue is purified by chromatography on silica gel (eluent: ethyl acetate/heptane/glacial acetic acid 40:20:1). 1.36 g of I are obtained as yellowish resin.

$^1$H-NMR (200 MHz, DMSO): δ=0.8 (2 s); 1.6–1.9 (m); 2.5–2.7 (m); 3.1–3.9 (m); 6.8 (s, overlapping with d, J=8 Hz); 7.1–7.6 (m); 7.75 (d, J=8 Hz); 8.3 (B); 12.5 (bs) ppm.

MS (FAB): m/e=547 (M+H+)

EXAMPLE II (Process B)

(±)-4-(3Z-(1H-Imidazo[4,5-b]pyridin-3-yl)-3-phenylpropenoyloxy)-2-(4-chlorophenylpropyloxy)-3,3-dimethylbutanoic acid (II)

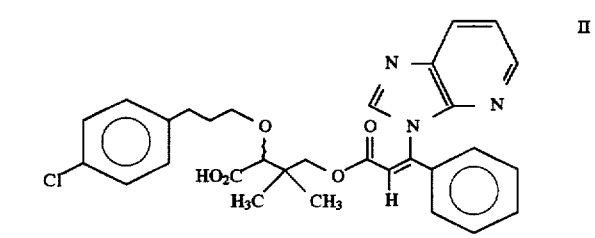

Stage 1

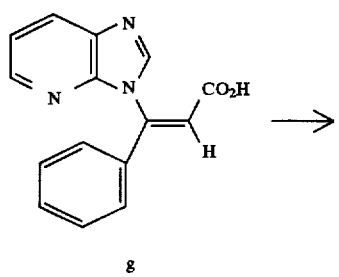

-continued

Stage 1

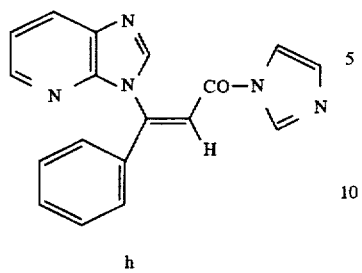

h

Compound h is prepared in analogy to Example 1, stage 4, from 1.8 g of compound g (compare process I, II or III for preparation) and used directly, without working up, in stage 2.

Stage 2

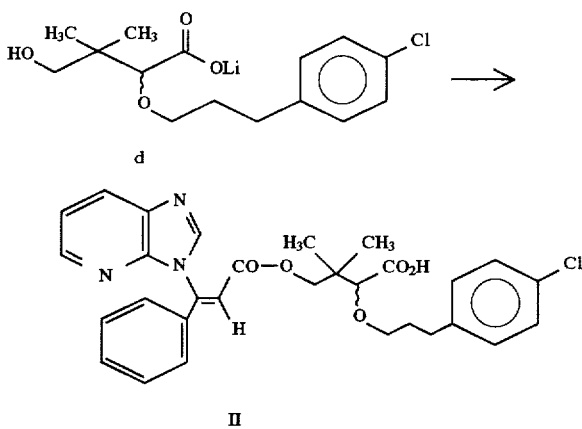

100 mg of 80 percent NaH in mineral oil are added to a solution of 0.95 g of compound d (compare Example 1, stage 1 to 3) in 20 ml of anhydrous DMF under argon, and the mixture is stirred at room temperature for 2 hours. The solution of compound h prepared in stage 1 is then added dropwise, and the mixture is stirred at room temperature for 25 hours. The reaction is followed by TLC (eluent: ethyl acetate/heptane/glacial acetic acid 30:30:1). For working up, the mixture is poured onto ice-cold saturated NH$_4$Cl solution and extracted several times with CH$_2$Cl$_2$. The organic phases are dried and evaporated and the residue is purified by chromatography on silica gel (eluent: ethyl acetate/ heptane/glacial acetic acid 10:50:1). Compound II is obtained as a yellowish resin. $^1$H-NMR (200 MHz, DMSO): δ=0.8 (s); 1.7 (m); 2.5 (m); 3.1–3.9 (m); 5.8 (s); 6.9 (s); 7.1–7.6 (m); 8.1 (m); 8.5 (s) ppm.

MS (FAB): m/e=548 (M+H$^+$)

EXAMPLE III (±)-4-(3Z-(1H-Imidazo[4,5-b]pyridin-3-yl)-3-phenylpropenoyloxy)-2-(4-chlorophenylpropyloxy) butanoic acid (III)

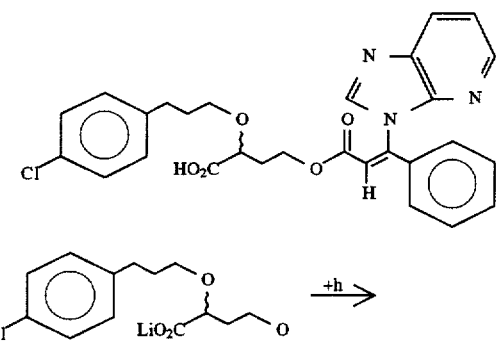

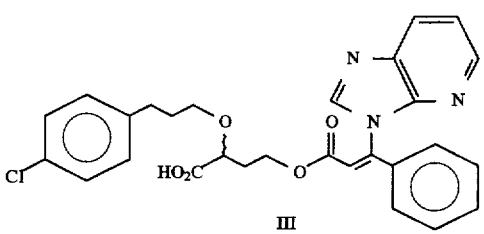

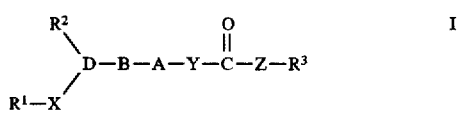

III

Compound i is prepared by an analogous reaction sequence like Example 1, stage 1 to 3, but (±)-α-hydroxybutyrolactone is used as starting material in place of DL-pantolactone.

100 mg of 80 percent NaH in mineral oil are added to a solution of 0.95 g of compound i in 20 ml of anhydrous DMF under argon, and the mixture is stirred at room temperature for 2 hours. The solution of compound h prepared from 1.8 g of compound g as in Example 2, stage 1, is then added dropwise and the mixture is stirred at room temperature for 25 hours. The reaction is followed by TLC (eluent: ethyl acetate/heptane/glacial acetic acid 30:30:1). For working up, the mixture is poured onto ice-cold saturated NH$_4$Cl solution and extracted several times with CH$_2$Cl$_2$. The organic phases are dried and evaporated, and the residue is purified by chromatography on silica gel (eluent: ethyl acetate/heptane/glacial acetic acid 30:30:1). Compound III is obtained as yellowish solid, melting point 95° C.

$^1$H-NMR (200 MHz, DMSO): δ=1.7 (m); 2.6 (m); 3.1–3.7 (m); 4.0 (t); 6.85 (5); 7.1–7.6 (m); 8.1–8.3 (m); 8.5 (s); 12.5 (bs) ppm.

Ms (fab): m/e=520 (M+H$^+$)

It is claimed:

1. A compound of the formula I $$\begin{array}{c} R^2 \\ \diagdown \\ R^1-X \end{array} D-B-A-Y-\overset{O}{\underset{\|}{C}}-Z-R^3 \quad I$$

in which:

X is (CH$_2$)$_m$;

m is zero;

D is CH;

B is CH$_2$, CH(CH$_3$), or C(CH$_3$)$_2$;

A is CH$_2$;

Y is O;

Z is (CH$_2$)$_m$ (m being 0, 1, 2, 3 or 4), S, O, S—C$_1$-C$_{10}$-alkyl (unbranched or branched), CH=CH, CH=CF, CH=CCl, CH=CBr, CH$_2$—C(O), CH$_2$—CHF, CH$_2$—CHCl, CH$_2$—CHBr, CH$_2$—CHI, C$_3$-C$_{10}$- cycloalkylene, $C_3$–$C_{10}$-cycloalkenylene, C≡C, CH=C($C_1$–$C_4$-alkyl) (unbranched or branched), CH=C(CN), CH=C($R^{10}$), or $NF^5$;

$R^1$ is CN, COOH, a COOH group protected by a protective group or $C_1$–$C_4$-alkanoyl or 5-tetrazolyl;

$R^2$ is O—$C_1$–$C_{10}$-alkyl($R^8$)$_n$ (n=0, 1, 2), where the alkyl moiety is unbranched, branched or cyclic, and one of the $CH_2$ groups can be replaced by O, and $R^8$ can be substituted by $R^9$, and, when n=2, the two $R^8$ radicals are identical or different, O—$C_3$–$C_{10}$-alkenyl ($R^8$), (n=0, 1, 2), where the alkenyl moiety is unbranched, branched or cyclic, one of the $CH_2$ groups can be replaced by O, S, SO, $SO_2$, or $NR^5$, and is mono- or polyunsaturated, and $R^8$ can be substituted by $R^9$, and, when n=2, the two $R^8$ radicals are identical or different, O—C3—$C_{10}$-alkynyl($R^8$), (n=0, 1, 2), where the alkynyl moiety is unbranched, branched or cyclic, and is mono- or polyunsaturated, and one of the $CH_2$ groups can be replaced by O, S, SO, $SO_2$, or $NR^5$, and $R^8$ can be substituted by $R^9$, and, when n=2, the two $R^8$ radicals are identical or different;

$R^3$, $R^8$, and $R^{10}$ are alkyl having 1 to 10 carbon atoms, cycloalkyl having 3–8 ring carbon atoms, phenyl, naphthyl, phenanthryl, pyridyl, thienyl, furyl, pyrimidyl, indolyl, imidazolyl, coumarinyl, phthalimidyl, quinolyl, piperazinyl, tetrazolyl, triazolyl, oxazolyl or their thieno-, pyridino-, pyrimidino-, pyrazino-, pyridazino- or benzo-fused derivatives, where the aromatic or heteroaromatic system can be substituted one or more times, identically or differently, by F, Cl, Br, I, OH, $CF_3$, —$NO_2$, CN, $C_1$–$C_4$-alkoxy, $C_1$–$C_4$-alkyl, $NR^5R^6$, phenyl, benzyl, thienyl, furyl, imidazolyl, pyridyl, —O-phenyl or —O-benzyl, and $R^3$, $R^8$ and $R^{10}$ are identical or different;

$R^4$ is $C_1$–$C_4$-alkyl, phenyl, or benzyl;

$R^5$ and $R^6$ are H, $C_1$–$C_4$-alkyl, $C_1$–$C_4$-alkanoyl, phenyl which is optionally substituted by F, Cl, Br, I, OH, O—$C_1$–$C_4$-alkyl, $CF_3$, —$NO_2$ or CN, where $R^5$ and $R^6$ are identical or different, or $R^5$ and $R^6$ form, together with the nitrogen atom, a 4- to 10-membered, saturated heterocyclic ring in which one $CH_2$ group can optionally be replaced by O, S or $NR^7$;

$R^7$: H, $C_1$–$C_4$-alkyl, phenyl or benzyl;

$R^9$: phenyl, naphthyl, phenanthryl, pyridyl, thienyl, furyl, pyrimidyl, indolyl, imidazolyl, coumarinyl, phthalimidyl, quinolyl, piperazinyl, tetrazolyl, triazolyl, oxazolyl or their thieno- or benzo-fused derivatives, where the aromatic or heteroaromatic system can be substituted one or more times, identically or differently, by F, Cl, Br, I, OH, $CF_3$, —$NO2$, CN, $C_1$–$C_4$-alkoxy, $C_1$–$C_4$-alkyl, $C_2$–$C_4$-alkenyl, $NR^5R^6$, phenyl, benzyl, thienyl, furyl, imidazolyl, pyridyl, O-phenyl or O-benzyl.

2. A compound as claimed in claim 1, wherein $R^3$, $R^8$, and $R^{10}$ are identical or different and are indolyl, imidazolyl or their benzo-fused derivatives.

3. A compound as claimed in claim 1, wherein E in formula I is substituted by 2 methyl groups.

4. (±)-4-(3Z-benzimidazol-1-yl-3-phenylpropenoyloxy)-2-(4-chlorophenylpropyloxy)-3,3-dimethylbutanoic acid.

5. (±)-4-(3Z-(1H-Imidazo[4,5-b]pyridin-3-yl)-3-phenylpropenoyloxy)-2-(4-chlorophenylpropyloxy)-3,3-dimethylbutanoic acid.

6. (±)-4-(3Z-(1H-Imidazo[4,5-b]pyridin-3-yl)-3-phenylpropenoyloxy)-2-(4-chlorophenylpropyloxy) butanoic acid.

7. A pharmaceutical composition for the treatment of diseases characterized by increased glucose-6-phosphatase activity comprising an amount of a compound as claimed in claim 1 effective to inhibit glucose-6-phosphatase activity.

8. A method of treating diseases characterized by increased activity of the glucose-6-phosphatase system comprising administering to a mammal in need thereof an effective amount of a compound of claim 1.

9. A method of treating type II diabetes comprising administering to a mammal in need thereof an effective amount of a compound of claim 1.

10. A method of treating diseases characterized by increased glucose production in the liver comprising administering to a mammal in need thereof an effective amount of a compound of claim 1.

* * * * *

UNITED STATES PATENT AND TRADEMARK OFFICE
CERTIFICATE OF CORRECTION

PATENT NO. : 5,767,141
DATED : June 16, 1998
INVENTOR(S) : Gerrit SCHUBERT et al.

It is certified that error appears in the above-identified patent and that said Letters Patent is hereby corrected as shown below:

Claim 1, column 19, line 3, "$NF^5$" should read --$NR^5$--.

Claim 1, column 19, line 10, "$(R^8)$," should read --$(R^8)_n$--.

Claim 1, column 19, line 16, "$O-C3-C_{10}$-alkynyl$(R^8)$," should read --$O-C_3-C_{10}$-alkynyl$(R^8)_n$--.

UNITED STATES PATENT AND TRADEMARK OFFICE
CERTIFICATE OF CORRECTION

PATENT NO. : 5,767,141
DATED : June 16, 1998
INVENTOR(S) : Gerrit Schubert et al.

It is certified that error appears in the above-identified patent and that said Letters Patent is hereby corrected as shown below:

Claim 1, column 19, line 18, "$CH_2$groups" should read --$CH_2$ groups--.

Claim 1, column 20, line 10, "-NO2" should read -- -$NO_2$--.

Claim 3, column 20, line 16, "E" should read --B--.

Signed and Sealed this

Thirteenth Day of July, 1999

Attest:

Attesting Officer

Q. TODD DICKINSON

Acting Commissioner of Patents and Trademarks